US00PP33974P2

(12) United States Plant Patent
Cain

(10) Patent No.: US PP33,974 P2
(45) Date of Patent: Mar. 1, 2022

(54) GRAPEVINE PLANT NAMED 'IFG FORTY-SEVEN'

(50) Latin Name: ***Vitis* interspecific hybrid**
Varietal Denomination: IFG Forty-seven

(71) Applicant: David Cain, Bakersfield, CA (US)

(72) Inventor: David Cain, Bakersfield, CA (US)

(73) Assignee: International Fruit Genetics, LLC., Bakersfield, CA (US)

( * ) Notice: Subject to any disclaimer, the term of this patent is extended or adjusted under 35 U.S.C. 154(b) by 0 days.

(21) Appl. No.: 17/300,420

(22) Filed: Jun. 24, 2021

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./205
CPC ..... A01H 6/88
See application file for complete search history.

*Primary Examiner* — Anne Marie Grunberg

(57) ABSTRACT

This invention is a new and distinct grapevine variety denominated 'IFG Forty-seven'. The new grapevine 'IFG Forty-seven' is characterized by producing small dark red berries having a broad ellipsoid shape with a unique strong fruity labrusca flavor reminiscent of artificial grape flavor. Fruits normally ripen in early season about late June to early July near Delano Calif. Fruits have medium to firm texture. Vines are productive and can be pruned to short spurs.

1 Drawing Sheet

Latin name of the genus and species claimed: *Vitis* interspecific hybrid.

Variety denomination: 'IFG Forty-seven'.

BACKGROUND OF THE INVENTION

The new and distinct grapevine described and claimed herein originated from a hand pollinated cross of IFG 05027-071-124, and IFG 05006-068-194, both unnamed interspecific selections from the IFG breeding program hybridized in May 2010. The abortive seed traces were subsequently embryo cultured and the resulting population of 17 plants was planted in the field in April 2011. The present variety of grapevine was selected as a single plant in June 2012 and was first asexually propagated by hardwood cuttings in December 2012 near Delano, Kern County, Calif. The resulting propagules were planted during April 2013 near Delano, Kern County, Calif. and were observed for five years and found to reproduce true-to-type through at least two generations of asexual reproduction.

BRIEF SUMMARY OF THE INVENTION

The new grapevine 'IFG Forty-seven' is characterized by producing small dark red berries having a broad ellipsoid shape with a unique strong fruity labrusca flavor reminiscent of artificial grape flavor. Fruits normally ripen in early season about late June to early July near Delano Calif. Fruits have medium firm texture. Vines are productive and can be pruned to short spurs. The new grapevine differs from its female parent the IFG 05027-071-124 by having a more broad ellipsoid rather than round berry shape; by having a larger, more dense cluster and by having a less notable muscat flavor and a stronger labrusca type flavor. 'IFG Forty-seven' can be distinguished from its pollen parent, IFG 05006-068-194, by having a darker red berry color, by having a larger cluster and by ripening approximately two weeks earlier. 'IFG Forty-seven' is most similar to 'IFG Thirty-one' (U.S. Plant Pat. No. 29,936 P2). It differs from 'IFG Thirty-one' by ripening approximately three weeks earlier, by having a brighter red berry color, and by exhibiting a lower propensity for tip cracking during ripening. 'IFG Forty-seven' is somewhat similar to 'Flame Seedless' (not patented), but differs by ripening earlier, by having a slightly softer berry texture, by developing a darker red berry color and by having a strong labrusca type flavor as opposed to the neutral flavor of 'Flame Seedless'. The new grapevine variety, 'IFG Forty-seven', is being introduced because of its unique labrusca flavor combined with seedlessness, good adhesion of skin to flesh and its earliness of ripening.

BRIEF DESCRIPTION OF THE DRAWING

The accompanying photographic drawing illustrates in full color a 5-year-old plant of 'IFG Forty-seven'. The photograph was taken outdoors with indirect lighting. The colors are as nearly true as is reasonably possible in a color representation of this type. The fruit depicted in the drawing is in its natural state and has not been treated with gibberellic acid. The drawing is of a mature leaf, a mature fruit cluster, a typical berry in cross section and a young shoot tip.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published in 2016 by The Royal Horticultural Society, London, England.

Throughout this specification, subjective description values conform to those set forth by the UPOV International Union for the Protection of New Varieties of Plants publication 'Grapevine *Vitis* L. Guidelines'.

The descriptive matter which follows pertains to 'IFG Forty-seven' plants grown in the vicinity of Delano, Kern County, Calif. during 2018 and 2019, and is believed to apply to plants of the variety grown under similar conditions of soil and climate elsewhere:

VINE

General:

*Vigor*.—Vigorous.
*Density of foliage*.—Dense.
*Productivity*.—Productive, producing about 14.1 to 21.2 kg of fruit per vine.
*Root stock*.—Own root.
*Training method*.—Typically spur pruned leaving 2 bud spurs.

Trunk:

*Trunk diameter of 5-year-old vines at 30 cm above the soil line*.—About 6.3 cm.
*Shape*.—Somewhat stocky.
*Surface texture*.—Shaggy texture.
*Inner bark color*.—The following colors were observed: Greyed-orange: 165A and 166A.
*Outer bark color*.—The following colors were observed: Brown: 200B and N200B.

SHOOTS

Young shoot:

*Form of tip*.—Fully opened.
*Distribution of anthocyanin coloration of tip*.—Absent.
*Intensity of anthocyanin coloration of tip*.—Absent.
*Density of prostrate hairs of tip*.—Medium to dense.
*Density of erect hairs on tip*.—Absent.
*Color*.—Yellow-green: N144A.

Woody shoot (mature canes):

*Internode length*.—Medium: About 9.8 cm.
*Width at node*.—About 1.2 cm.
*Cross section*.—Circular.
*Surface*.—Striate.
*Main color*.—The following colors were observed: Greyed-orange: 165A and 165B and 165C.
*Density of erect hairs on nodes*.—None.
*Density of erect hairs on internodes*.—None.
*Axillary shoot length at full bloom*.—Weak: Approximately 11.0 cm.

Flowering shoot:

*Vigor during flowering*.—Very strong.
*Attitude during flowering on shoots not tied*.—Semi-erect.
*Color*.—Dorsal side of internodes — Yellow-green: 144A, with Red-purple stripes: 187A.
*Color*.—Ventral side of internodes — Yellow-green: 144A.
*Color*.—Dorsal side of nodes — Yellow-green: 144A.
*Color*.—Ventral side of nodes — Yellow-green: 144A.
*Density of prostrate hairs on nodes*.—Medium to dense.
*Density of erect hairs on nodes*.—None.
*Density of prostrate hairs on internode*.—Medium.
*Density of erect hairs on internode*.—None.
*Anthocyanin coloration of buds*.—Absent.

Tendrils:

*Distribution on the shoot (at full flowering)*.—Discontinuous.
*Length of tendril*.—Long: About 37.6 cm.
*Thickness of tendril 2 cm from base*.—About 2.2 mm.
*Color*.—Yellow-green: 144C.
*Form*.—Bifurcated.
*Number of consecutive tendrils*.—2.

LEAVES

Young leaves:

*Color of upper surface of first four distal unfolded leaves*.—Yellow-green: 144A.
*Color of lower surface of young leaves*.—Yellow-green: 144A.
*Average intensity of anthocyanin coloration of six distal leaves prior to flowering*.—Absent.
*Density of prostrate hairs between veins (lower surface)*.—Medium to dense.
*Density of prostrate hairs on veins (lower surface)*.—Dense.
*Density of erect hairs between veins (lower surface)*.—Absent.
*Density of erect hairs on veins (lower surface)*.—Very sparse.

Mature leaves (opposite first cluster):

*Average length*.—About 16.1 cm.
*Average width*.—About 18.2 cm.
*Mature leaf size*.—Large.
*Shape of blade*.—Wedge-shaped.
*Number of lobes*.—5.
*Blade venation*.—Palmate.
*Anthocyanin coloration of main veins on upper side of blade*.—Absent.
*Mature leaf profile*.—Flat.
*Blistering surface of blade upper surface*.—Weak.
*Leaf blade tip*.—In the plane of the leaf.
*Leaf apex*.—Acute.
*Leaf margin*.—Serrate.
*Undulation of margin*.—Slight.
*Undulation of blade between main and lateral veins*.—Absent.
*Shape of teeth*.—Mixture of both sides straight and both sides convex.
*Average length of teeth*.—Short: About 0.4 cm.
*Average width of teeth*.—Medium: About 0.8 cm.
*Ratio length/width of teeth*.—Medium.
*Shape of upper lateral sinuses*.—Lobes slightly overlapping.
*Depth of upper lateral sinuses*.—Shallow: About 2.3 cm.
*General shape petiole sinus*.—Half open.
*Shape of base of upper leaf sinuses*.—U-shaped.
*Tooth at petiole sinus*.—Absent.
*Density of prostrate hairs between veins on lower surface of blade*.—Medium.
*Density of erect hairs between veins on lower surface of blade*.—Absent.
*Density of prostrate hairs on main veins on lower surface of blade*.—Medium.
*Density of erect hairs on main veins on lower surface of blade*.—Sparse.
*Density of prostrate hairs on main veins on upper surface of blade*.—Sparse.

*Density of erect hairs on main veins on upper surface of blade*.—None or very sparse.

*Autumn coloration of leaves*.—Leaves can be a single color or combination of colors, in a mottled pattern or on the edges of the leaves. The following colors were observe: Greyed-yellow: 162A and 162B.

Upper surface:

*Color*.—Green: 137A.

*Anthocyanin coloration of main veins* (*lower surface*) .—Absent.

*Color of main veins*.—Yellow-green: 144B.

*Surface appearance*.—Dull.

*Blistering surface of blade*.—Weak.

Lower surface:

*Color*.—Yellow-green: 146A.

*Anthocyanin coloration of main veins* (*lower surface*).—Absent.

*Color of main veins*.—Yellow-green: 145B.

*Glossiness*.—Weak.

*Surface texture*.—Smooth.

*Surface appearance*.—Dull.

Petiole:

*Length*.—About 13.7 cm.

*Diameter of petiole* 2 *cm from blade*.—About 3.3 mm.

*Petiole color*.—Yellow-green: 144B.

*Length of petiole compared to middle vein*.—Slightly shorter.

*Density of prostrate hairs on petiole*.—None or very sparse.

*Density of erect hairs on petiole*.—None.

Buds:

*Bud fruitfulness*.—Basal: mostly fruitful.

*Position of first fruitful shoot on previous season cane*.—$1^{st}$ to $2^{nd}$ node.

*Dormant bud length*.—About 5.5 mm.

*Dormant bud width in the proximal/distal plane*.—About 4.8 mm.

*Dormant bud color*.—Greyed-orange: 165A and 165B.

*Time of bud burst*.—Midseason; about Mar. 15, 2019.

FLOWERS

General:

*Flower sex*.—Hermaphrodite.

*Length of single flower, unopened*.—About 3.6 mm.

*Width of single flower*.—Unopened: About 2.3 mm. Opened: About 7.8 mm.

*Stamen length*.—About 5.6 mm.

*Stamen count*.—5.

*Pollen color*.—Yellow: 10B.

*Pistil length*.—About 2.7 mm.

*Pistil color*.—Yellow-green: 144A.

*Length of first inflorescence*.—Medium: About 15.4 cm long by 7.8 cm wide.

*Position of first flowering and fruiting node*.—$2^{nd}$ to $4^{th}$ (current season growth).

*Number of inflorescences per flowering shoot*.—1.1 to 2: About 2.0.

*Time of bloom*.—Medium as compared with similar varieties in the growing area of Delano, Calif.

*Date of full bloom*.—About May 5, 2019.

FRUIT

General:

*Ripening period*.—Early: Approximately Jul. 18, 2018.

*Use*.—Fresh market.

*Keeping quality*.—Average, remains commercially acceptable when stored for several weeks at 0° C. and high relative humidity.

*Refractometer test*.—Soluble solids: About 18.0 Brix.

*Brix/acid*.—About 33.3.

*Titratable acidity*.—About 0.54.

*Juice ph*.—About 3.9.

*Juice color*.—Greyed-orange: 173D.

Cluster:

*Mature cluster length* (*peduncle excluded*).—About 20.4 cm.

*Mature cluster width*.—About 13.8 cm.

*Mature cluster weight*.—About 471.4 g.

*Bunch density*.—Loose to medium: densely distributed berries with single berries, and few to some pedicels visible, berries are movable.

*Number of berries*.—About 158.

*Form*.—Conical.

Peduncle:

*Lignification of peduncle*.—Weak.

*Diameter of peduncle*.—Approximately 5.7 mm.

*Length of peduncle*.—Short: Approximately 2.5 cm.

*Color of peduncle*.—Yellow-green: 145A.

Berry:

*Uniformity of size*.—Uniform.

*Single berry weight*.—About 3.5 g natural; to about 5.5 g when treated with gibberellic acid.

*Shape*.—Broad ellipsoid.

*Seeds*.—Contains small rudimentary seed traces.

*Cross section*.—Circular.

*Berry dimensions*.—Longitudinal axis: About 18.7 mm: Horizontal axis: About 16.9 mm.

*Pedicel length*.—About 7.0 mm.

*Pedicel width*.—About 1.5 mm.

*Pedicel color*.—Yellow-green: 145A.

*Berry firmness*.—Medium to firm.

*Particular flavor*.—Spicy labrusca.

*Bloom* (*cuticular wax*).—Medium to strong.

*Berry separation from pedicel*.—Medium.

*Skin color* (*without bloom*).—The following colors were observed: Greyed-purple: N186B and N186C.

*Flesh color*.—Green-white: 157B.

Skin:

*Thickness*.—Medium.

*Skin toughness*.—Not notable when chewing.

*Reticulation*.—Absent.

*Tenacity*.—Tenacious to flesh.

What is claimed:

1. A new and distinct variety of grapevine plant as herein illustrated and described.

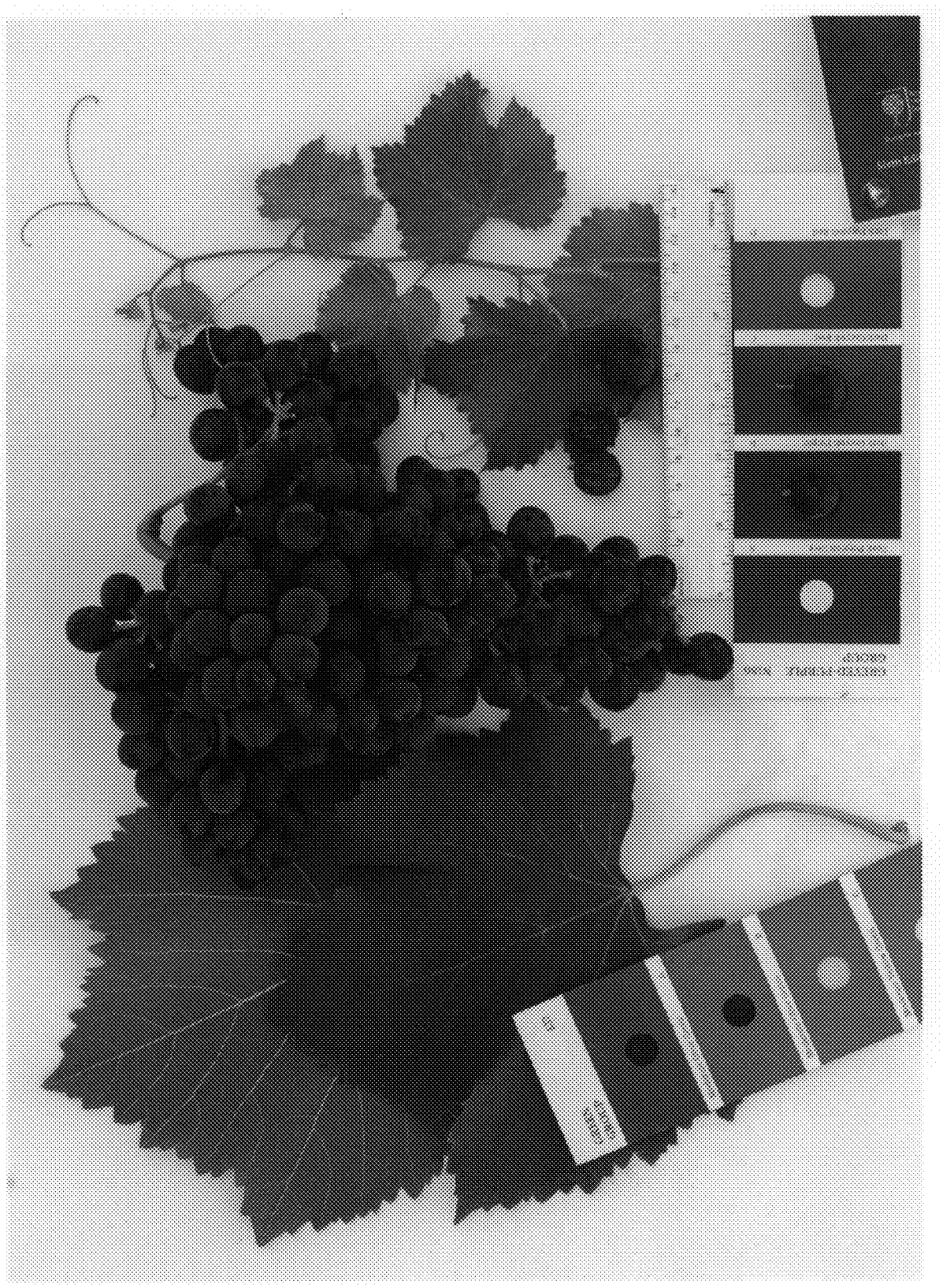

* * * * *